(12) United States Patent
Shibuya et al.

(10) Patent No.: US 7,671,339 B2
(45) Date of Patent: Mar. 2, 2010

(54) POSITRON EMISSION TOMOGRAPHY SCANNER AND RADIATION DETECTOR

(75) Inventors: Kengo Shibuya, Chiba (JP); Tomoaki Tsuda, Uji (JP); Fumihiko Nishikido, Chiba (JP); Naoko Inadama, Chiba (JP); Eiji Yoshida, Chiba (JP); Taiga Yamaya, Chiba (JP); Hideo Murayama, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 482 days.

(21) Appl. No.: 11/658,699

(22) PCT Filed: Dec. 25, 2006

(86) PCT No.: PCT/JP2006/026357

§ 371 (c)(1),
(2), (4) Date: Jan. 29, 2007

(87) PCT Pub. No.: WO2008/023451

PCT Pub. Date: Feb. 28, 2008

(65) Prior Publication Data

US 2009/0159804 A1    Jun. 25, 2009

(30) Foreign Application Priority Data

Aug. 25, 2006  (JP)  ............................ 2006-229376

(51) Int. Cl.
*G01T 1/164*  (2006.01)
*G01T 1/166*  (2006.01)

(52) U.S. Cl. .............................. 250/363.03; 250/363.04

(58) Field of Classification Search ............ 250/363.03, 250/363.04
See application file for complete search history.

(56) References Cited

U.S. PATENT DOCUMENTS 7,411,197 B2 * 8/2008 He et al. ................. 250/370.01
2008/0103391 A1 * 5/2008 Dos Santos Varela ....... 600/436
2008/0237475 A1 * 10/2008 Michaud et al. ......... 250/363.03

FOREIGN PATENT DOCUMENTS

JP      A-11-142523      5/1999

(Continued)

OTHER PUBLICATIONS

Moses W., "Time of Flight in PET Revisited," Oct. 2003, IEEE Transactions on Nuclear Science, vol. 50, No. 5, pp. 1325-1330.

(Continued)

*Primary Examiner*—David P Porta
*Assistant Examiner*—Mindy Vu
(74) *Attorney, Agent, or Firm*—Oliff & Berridge, PLC (57) ABSTRACT

A positron emission tomography (PET) scanner is provided which uses information on the time-of-flight difference (TOF) between annihilation radiations for image reconstruction. The scanner has detection time correction information (memory) corresponding to information on coordinates in a radiation detection element (e.g., scintillator crystal), in the depth and lateral directions, at which an interaction has occurred between an annihilation radiation and the crystal. Reference is made to the detection time correction information, thereby providing information on time-of-flight difference with improved accuracy. As such, an improved signal to noise ratio and spatial resolution are provided for image reconstruction using time-of-flight (TOF) difference.

10 Claims, 9 Drawing Sheets

FOREIGN PATENT DOCUMENTS

| | | |
|---|---|---|
| JP | A-2004-132930 | 4/2004 |
| JP | A 2004-279057 | 7/2004 |
| JP | A-2004-279057 | 10/2004 |
| JP | A-2005-017142 | 1/2005 |
| JP | A-2005-043062 | 2/2005 |
| JP | A-2005-043104 | 2/2005 |
| WO | WO 2004/090572 A1 | 10/2004 |
| WO | WO 2004/095068 A1 | 11/2004 |

OTHER PUBLICATIONS

Tomitani T., "Image Reconstruction and Noise Evaluation in Photon Time-Of-Flight Assisted Positron Emission Tomography," Dec. 1981, IEEE Transactions on Nuclear Science, vol. NS-28, No. 6, pp. 4582-4589.

Tsuda T. et al., "Performance Evaluation of a Subset of a Four-Layer LSO Detector for a Small Animal DOI PET Scanner: jPET-RD," Feb. 2006, IEEE Transactions on Nuclear Science, vol. 53, No. 1, pp. 35-39.

"Radiation Detection and Measurement," 2000, John & Wiley Sons, Inc., $3^{rd}$ Edition, p. 662.

Shibuya, K, et al., "Fast Radiation Detectors for Time-of-Flight Positron Emission Tomography (TOP-PET)" in Radioisotopes, vol. 55, No. 7, pp. 391-402.

Moses, W, W, et al. "Prospects for Time-of-Flight Pet using LSO Scintillator" in IEEE Transactions on Nuclear Science NS-46, pp. 474-478.

* cited by examiner

POSITRON EMISSION TOMOGRAPHY SCANNER AND RADIATION DETECTOR

TECHNICAL FIELD

The present invention relates to a positron emission tomography (PET) scanner which uses information on the time-of-flight difference between the two annihilation radiations for image reconstruction, and to a radiation detector. More particularly, the invention relates to a positron emission tomography scanner which can determine the time of incidence of each radiation with improved accuracy, and a radiation detector which can be used therefore in a preferred manner.

BACKGROUND ART

The positron emission tomography scanner is a nuclear diagnostic imaging system which utilizes a positron emitter and finds widespread applications such as cancer diagnosis or molecular imaging.

A positron emitter is an isotope, such as $^{18}F$, which is unstable because of excess number of protons in the atomic nucleus against the number of neutrons, and which undergoes +β decay to emit a positron and a neutrino. The positron thus emitted is the antimatter counterpart of the electron. Accordingly, when the positron encounters an electron, they annihilate each other causing their mass to be entirely converted into energy. This energy is released in the form of annihilation radiation or high-energy electromagnetic wave. Since the law of conservation of momentum is obeyed before and after the pair annihilation, two annihilation radiations are principally emitted concurrently at an angle of about 180 degrees. In a strict sense, a single radiation or three or more radiations may also be emitted; however, they are less than 1% of the total radiations and thus can be ignored for imaging purposes. The respective energy of the two emitted radiations corresponds to the mass of one electron (or positron), i.e., approximately 511 keV.

Figure 1:
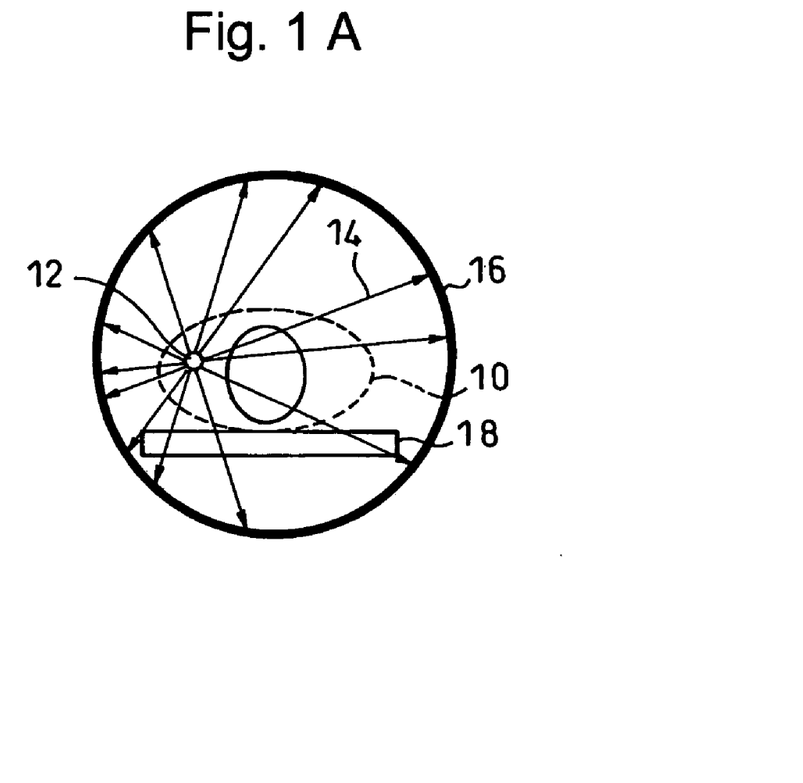

The principle of positron imaging is based on the coincidence measurement of the two annihilation radiations. When a radiation of 511 keV is detected substantially simultaneously at two oppositely disposed radiation detectors, this indicates that a positron has undergone a pair annihilation on the straight line connecting the two radiation detectors. As shown in FIG. 1A, this information is collected with a number of radiation detectors 16 disposed around a subject 10, and reconstructed by the similar mathematical technique to X-ray CT. A tomographic video or static image is thus provided that approximates the distribution of positron emitters 12 in the subject 10. In the figure, reference numeral 18 denotes a bed.

Accordingly, the performance required of the radiation detector 16 is to be capable of measuring the position of incidence, energy, and incidence time of an annihilation radiation 14 with the highest accuracy. As used herein, the expression "substantially the same time (simultaneously)" refers to points in time approximately within 15 nanoseconds (nano denotes $10^{-9}$). These points in time may also fall within 10 nanoseconds or less or 5 nanoseconds or less when the radiation detector can determine time with higher accuracy. A frame of time (or time window) may be reduced in which two annihilation radiations are determined to be incident at the same time and a single pair of annihilation radiations resulting from one electron-positron-pair annihilation. This would reduce the possibility of erroneously combining a plurality of annihilation radiations resulting from separate pair annihilations, namely accidental coincidence, thereby improving measurement accuracy and signal to noise ratios. It should be noted that although the temporal resolution of each radiation detector can currently be improved up to about 0.3 nanoseconds, those time windows reduced accordingly but excessively would reject the counting of true combinations of annihilation radiations, and also cause the field of view covered by the scanner to be narrowed with its sensitivity reduced.

Suppose that an electric signal from the radiation detector 16 can be processed to determine the time of incidence of the annihilation radiation 14 generally within 15 nanoseconds or less. In such a case, as is known to those skilled in the art, time-of-flight (TOF) difference between annihilation radiations can be used to improve the signal to noise ratio of the positron emission tomography scanner, maintaining the time window not rejecting the counting of true combinations of annihilation radiations. As an example, when a pair annihilation occurs at the center of two oppositely disposed radiation detectors, the two annihilation radiations arrive at the radiation detectors at the same time. On the other hand, when a pair annihilation occurs at coordinates (spatial coordinates) closer to either one of the radiation detectors, an annihilation radiation arrives at the closer radiation detector earlier than at the other. That is, the difference in arrival time between the radiations arriving at the respective radiation detectors can be determined and thereby converted into the difference in distance between the spatial coordinates at which the pair annihilation has occurred and the respective radiation detectors. In a conventional PET scanner, shown in FIG. 1A, which does not make use of the time-of-flight difference, the information obtained from a pair of coincidence measurements provides a straight line containing the spatial coordinates on which the pair annihilation is supposed to have occurred. However, use of the time-of-flight difference as with a time-of-flight difference type PET (TOF-PET) scanner shown in FIG. 1B narrows the special coordinate uncertainty to a certain confined range on the straight line. The accuracy of this confinement depends on the temporal resolution of the scanner, so that as the accuracy of determination is increased, the amount of information regarding the location of the pair annihilation is increased thereby providing an improved signal to noise ratio (see W. W. Moses, IEEE Trans. Nucl. Sci., Vol. 50, No. 5, pp. 1325-1330, 2003).

Note that if the time of incidence of an annihilation radiation can be determined generally within 100 picoseconds or less (pico denotes $10^{-12}$), it can be expected that not only the signal to noise ratio but also the spatial resolution of tomographic video or static images will be improved.

The concept of the TOF-PET scanner that makes use of the time-of-flight difference. between annihilation radiations was already known in the 1980s (see T. Tomitani, IEEE Trans. Nucl. Sci., Vol. 28, No. 6, pp. 4582-4589, 1981). However, at that time, the level of technological sophistication was insufficient to improve signal to noise ratios due to the inadequate performance of the scintillator crystals used as radiation detection elements, radiation detectors, and circuits for processing electric signals from radiation detectors. Today, scintillator crystals with good response speeds have been developed, such as LSO (lutetium oxyorthosilicate doped with a trace amount of cerium) or LYSO (a mixed crystal of LSO and yttrium oxyorthosilicate doped with a trace amount of cerium). In addition, the timing performance of a photomultiplier tube (PMT) that is used as an optical detector for detecting scintillation light produced through an interaction with radiations has also been improved. Furthermore, the application-specific integrated circuit technology has also advanced. It has been thus recognized that the TOF-PET scanner that makes use of the time-of-flight difference between annihilation radiations offers a performance advantage over the conventional PET scanner in its signal to noise ratio. Accordingly, there is an increasing need for a radiation detector that has an advantageous temporal resolution. An improvement in signal to noise ratio makes it possible to reduce the acquisition time required for positron emission tomography and the amount of radioactive pharmaceutical dosed to a subject.

Figure 2:
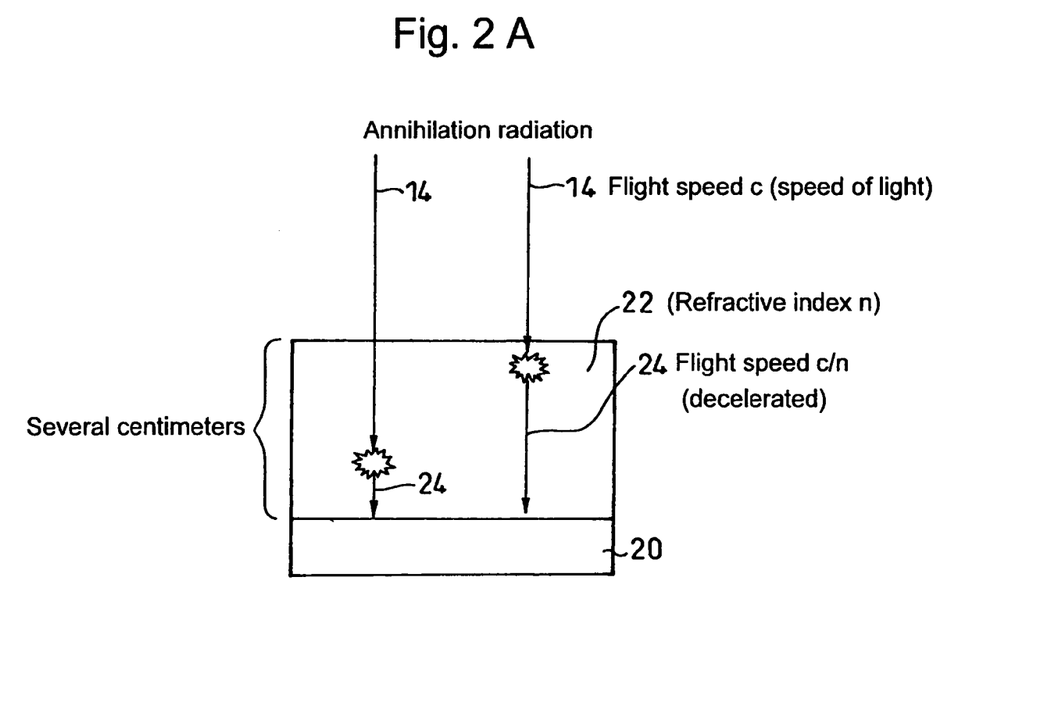

As shown in FIG. 2, a first cause of the error in detection time results from a difference in propagation speed in a scintillator crystal 22 between the annihilation radiation 14 and scintillation light 24. In the figure, reference numeral 20 denotes an optical detector such as a photomultiplier tube.

In the air as well as in the crystal, the flight speed of the annihilation radiation 14 is substantially the same as the speed of light c in a vacuum (299,800 km per second). In contrast, the scintillation light 24 travels at a speed of about c, in the air, but at a reduced speed of c/n in the crystal, where n is the refractive index of the crystal, which is typically greater than 1.0. To efficiently detect an annihilation radiation of 511 keV which has a great penetration power, a scintillator crystal 22, which is about a few centimeters in thickness, is typically employed.

As shown to the right of FIG. 2A, when the annihilation radiation 14 interacts with the scintillator crystal 22 near the top of the scintillator crystal 22, the scintillation light 24 has to travel longer through the scintillator crystal 22 to reach the optical detector 20. In contrast, as shown to the left of FIG. 2A, when an interaction occurs near the bottom of the scintillator crystal 22, the scintillation light 24 travels a correspondingly short distance to reach the optical detector 20. That is, as shown in FIG. 2B, an earlier apparent detection time is observed when the annihilation radiation 14 travels a longer distance through the scintillator crystal 22 still at a flight speed of c and is then converted immediately before the optical detector 20 into the scintillation light 24 traveling at a slower flight speed of c/n.

Assuming that when measuring a pair of annihilation radiations respectively with two radiation detectors, one optical detector detects scintillation light produced near the top of the scintillator crystal, whereas the other optical detector detects scintillation light produced near the bottom of the scintillator crystal. In such a case, the spatial coordinates of the pair annihilation estimated from the difference between the detection times are closer to the latter radiation detector than the actual location. Accordingly, a correction can be made to the error in detection time caused by the difference in propagation speed between the annihilation radiation and the scintillation light in the scintillator crystal, thereby providing information on time-of-flight difference with improved accuracy. It should be noted that for simplicity in illustration of the principle, FIG. 2A shows one typical scintillation photon emitted directly below per one pair annihilation radiation. However, in practice, several thousands to several tens of thousands of photons are emitted not only directly below but also in other directions. In addition, since some photons are absorbed on the boundary of the scintillator crystal or a reflective material or the like, not all photons reach the optical detector.

Figure 3:
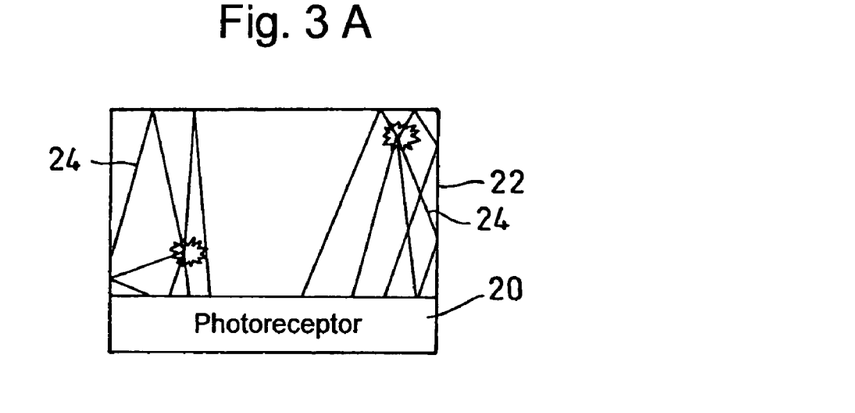

As illustrated in FIG. 3A, a second cause of the error in detection time results from a difference in path length in the scintillator crystal 22 along which the scintillation light 24 travels. Although part of the scintillation light 24 is directly incident upon the optical detector 20, generally half or more of the photons are reflected off on the upper surface or sides of the scintillator crystal 22 more than once and then incident upon the optical detector 20. For example, as shown to the right of FIG. 3A, a portion of the scintillation light 24 produced and emitted upwardly near the top of the scintillator crystal 22 arrives immediately at the top of the scintillator crystal 22, where it is reflected downwardly by a reflective material covering the upper surface of the scintillator crystal 22. In contrast, as shown to the left of FIG. 3A, the scintillation light 24 emitted upwardly near the bottom of the scintillator crystal 22 travels the length of the scintillator crystal 22 until it is reflected downwardly from the top of the scintillator crystal 22. Moreover, the scintillation light 24 emitted sideward at an angle travels a different propagation path depending on how it is reflected on a side of the scintillator crystal. Furthermore, when the scintillator crystal is arranged two- or three-dimensionally up/down, right/left, or forward/backward, the scintillation light 24 may take a more complex propagation path depending on how it is reflected or refracted between those scintillator crystals. In circumstances with a longer propagation path, the scintillation light 24 takes a longer time to reach the optical detector 20, thereby causing the time to be delayed at which it is determined that the annihilation radiation has been detected.

FIG. 3B shows the calculated results of a propagation path of scintillation light and its propagation time in a crystal block, where the crystal block has four layers to increase the detection accuracy of the location of an interaction between an annihilation radiation and a scintillator crystal. In this arrangement, one layer includes a square array of 32×32 LSO crystals each being 1.45 mm×1.45 mm×4.50 mm in size. To aid simplicity in illustrating the principle, the figure shows the relation between the number of photons reaching the optical detector and the elapse time, assuming that one crystal at the center of each layer is selected, and that at a reference time, one hundred thousand photons are emitted in random directions from the center of the respective crystals. Depending on the linear distance between the coordinates of the light emission in a scintillator crystal emitting light and the optical detector, the time when the first photons reaching the optical detector and the time at which photons are the largest in number are varied. Further, the time of second peak, which is caused by the reflection on the upper surface of the crystal, is varied depending on the distance. A correction can be made to the error in detection time caused in the above-described manner by the difference in propagation path length of scintillation light, thereby providing information regarding time-of-flight difference with improved accuracy.

A third cause of the error in detection time results from the difference in output waveform of an optical detector caused by a difference in propagation path. As can be seen from FIG. 3B which shows the distribution of times at which light (input) arrives at the optical detector, the time required from the arrival of the first photon from each crystal until the arrival of the greatest number of photons differ depending on the crystal. It is also evident from the shapes of the graphs that the number of photons tends to increase differently with time.

To most simply determine the time from the output waveform of the optical detector, a threshold value is first set in order to discriminate signals from noises, whereupon an output that exceeds the threshold value is defined as a signal so that the time at which the threshold value is exceeded is taken as the detection time. As shown in FIG. 3C, however, the threshold value is immediately exceeded after the arrival of the first photon when the output signal is comparatively high (e.g., the 4th layer), while when the output signal is comparatively low (e.g., the 1st layer), the threshold value is only exceeded near the time at which the output is at maximum. Thus, the time to be determined varies according to the signal magnitude. Accordingly, in practice, a further sophisticated determination method such as the constant fraction method is widely employed in order to avoid variations in the time irrespective of the magnitude of the output signal (see Radiation Detection and Measurement, 3rd Edition, p. 662, 2000, published by John and Wiley & Sons, Inc.).

However, although the constant fraction method can accommodate variations in the magnitude of output signals, it cannot accommodate variations in the waveform of output signals. Thus, the time to be determined varies depending on whether the signal rises sharply or gradually. Accordingly, a correction can be made to the error in detection time resulting from the difference in output waveform of an optical detector caused by the difference in propagation path of scintillation light, thereby providing information regarding time-of-flight difference with improved accuracy. This is also applicable not only to the constant fraction method but also other timing determination method such as the leading edge method. By way of example, a correction can be made in accordance with the gradient of the rise of a signal or also with a change in gradient.

Figure 4:
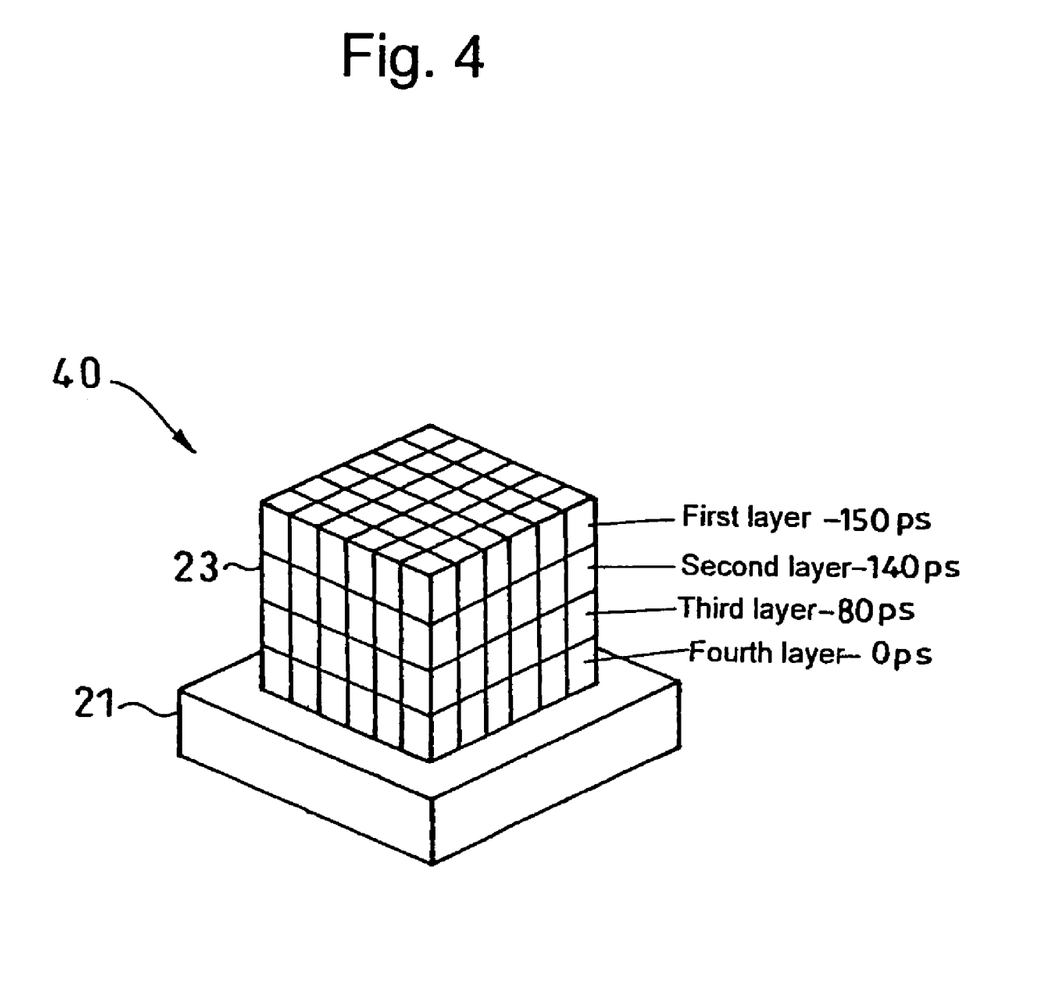
FIG. 4 is a perspective view for explaining one conventional solution.

It should be noted that a technique is already known which employs not the information regarding a three-dimensional location (emission location) but only the information regarding the location of emission in the direction of depth for a radiation detector as shown in FIG. 4 to make a correction to detection time (see T. Tsuda et al, IEEE Trans., Nucl. Sci., Vol. 53, No. 1, pp. 35-39, 2006). In the figure, reference numeral 40 denotes a radiation detector (also referred to as a DOI radiation detector) which is capable of obtaining information regarding the location of a depth of interaction (DOI). The radiation detector 40, which was suggested by the applicant in Japanese Patent Laid-Open Publication No. 2004-279057 (Patent Document 1), includes, e.g., a 256-channel position sensitive photomultiplier tube (PS-PMT) 21 and a 6×6 four-layered scintillator crystal block 23.

However, using only the information regarding the location of emission in the direction of depth may lead to an inaccurate correction. As shown in FIG. 2, if only one photon is emitted directly below, the location of emission in depth may be the sole cause of the error. However, in practice, a number of photons are reflected on the upper and side surfaces, and thus behave differently before they reach the optical detector depending on the effects of adjacent crystals and the distance to the sides of the crystal block. As already discussed, this may cause those errors to be produced which result from the difference in propagation path length of scintillation light and the difference in output waveform of an optical detector caused by the difference in propagation path of scintillation light.

DISCLOSURE OF INVENTION

The present invention was developed to address the aforementioned conventional problems. The invention relates to a technique, applied to a PET scanner, for determining the time of incidence of a radiation with improved accuracy. More particularly, an object of the present invention is to provide an improved signal to noise ratio and a spatial resolution for image reconstruction using time-of-flight difference.

The errors in detection time presented as problems are caused by the difference in propagation speed between an annihilation radiation and a scintillation light; the difference in propagation path length of scintillation light; and the difference in output waveform of an optical detector resulting from the difference in propagation path length of scintillation light. Each of the errors can be corrected for using the coordinates (crystal coordinates) that represent the location of a scintillation crystal at which an interaction has occurred between an annihilation radiation and the scintillator crystal.

Figure 5:
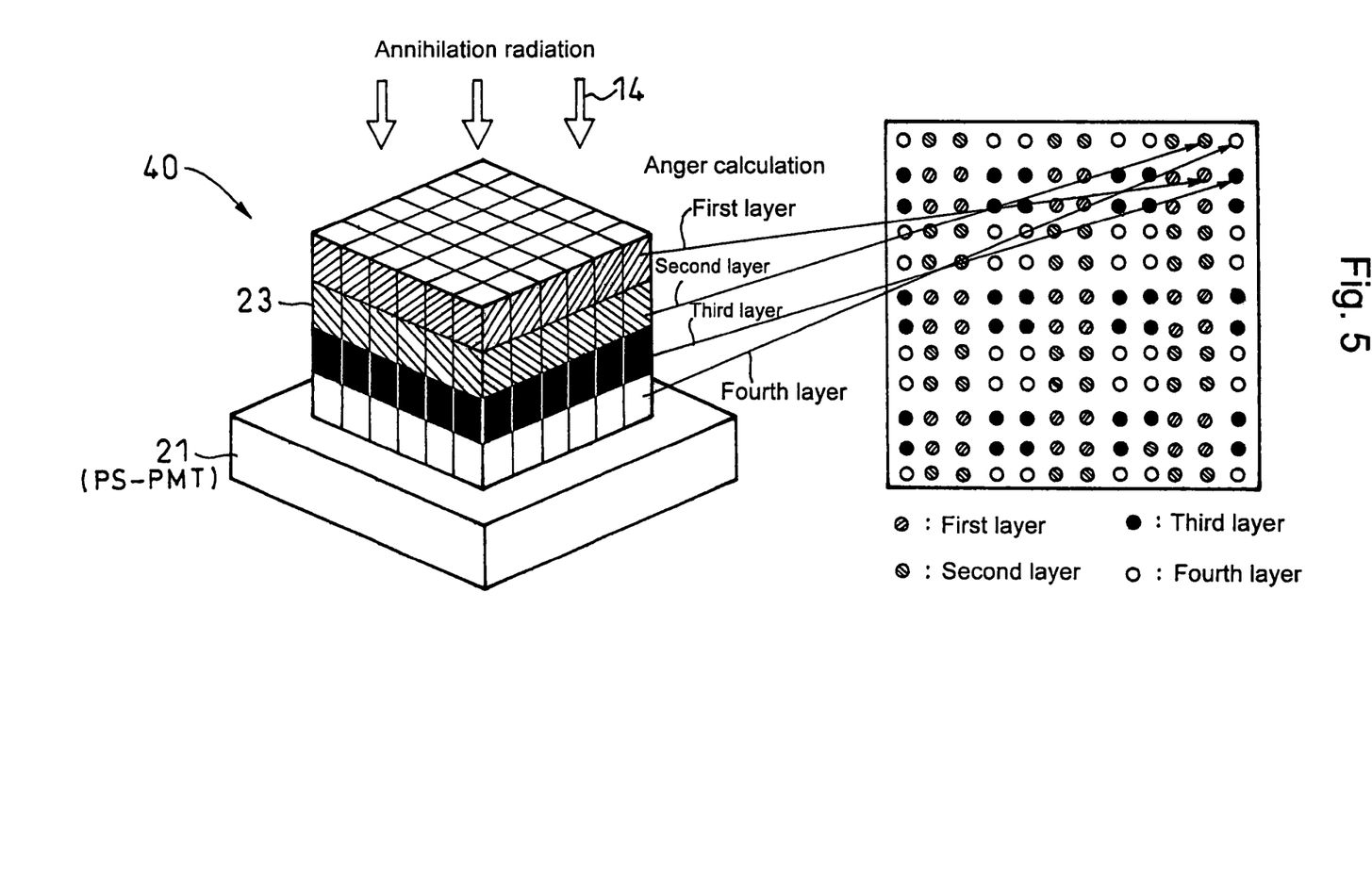
FIG. 5 is an explanatory view illustrating the principle of a solution according to the present invention.
Figure 6:
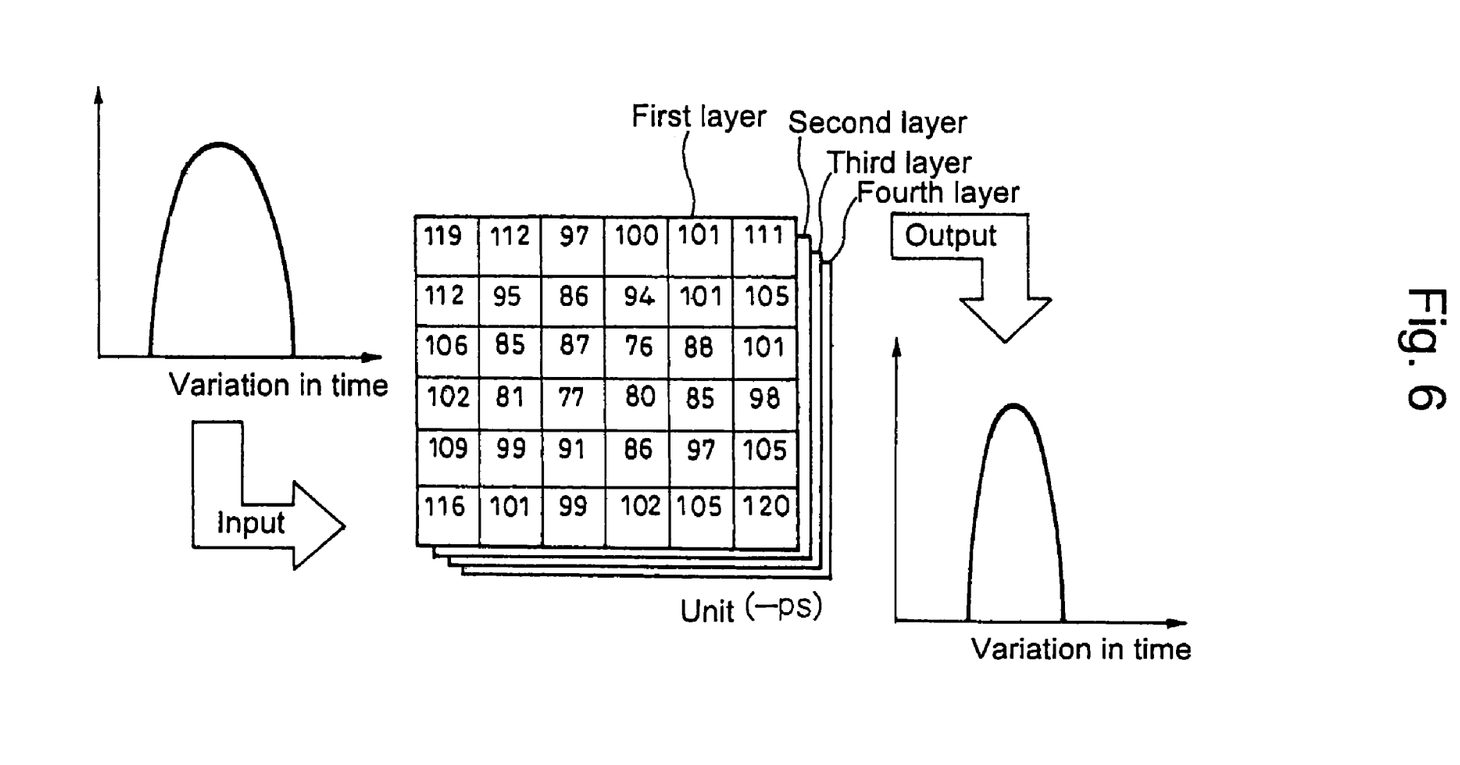
FIG. 6 is a view illustrating the principle.

For example, suppose that the DOI radiation detector 40 described in Patent Document 1 is used which has the three-dimensionally integrated crystal block 23 shown in FIG. 4 and FIG. 5. In this case, as shown in FIG. 6, a correction time for each of the individual crystal elements is predetermined to add or subtract this correction value to/from the time determined by measurement, thereby correcting for an error. These error data are stored in memory. For example, the data may be held in a ROM as the memory to make a correction by hardware such as a circuit used for signal processing, or may also be held in a hard disc drive as the memory to make a correction to digitized data by software. Alternatively, the data may also be written in a RAM or the like as required.

In a radiation detector of the PET scanner, the combination of a scintillator crystal and an optical detector does not always have a one-to-one correspondence. Thus, in general, such a scanner holds data for estimating the coordinates of a light emitting crystal from the output signal(s) of an optical detector(s). As an example, in the prototype head scanner jPET-D4 developed by National Institute of Radiological Sciences in JAPAN, the data are referred to as the two-dimensional location histogram which provides a one-to-one correspondence between the information on a two-dimensional output location obtained from output signals through the anode electrodes of a photomultiplier tube used as an optical detector and an individual crystal in the three-dimensionally integrated crystal block. A look-up table having this location histogram stored in memory is referenced for each event to identify the crystal that has emitted light. Then, the data on the crystal coordinates and the time is sent to subsequent coincidence measurement and decision circuits. Here, such a mechanism may be added in which time error data is held in consistency with the look-up table of information on crystal coordinates or a look-up table prepared separately, and after the crystal is identified, reference is made to the time error data to rewrite the time. This would make it possible to realize a PET scanner that provides information regarding time-of-flight difference with improved accuracy.

The present invention was developed based on the results of those studies to provide a positron emission tomography scanner which employs information regarding the time-of-flight difference between annihilation radiations for image reconstruction. The scanner has detection time correction information corresponding to information on the coordinates, representing both the depth direction and the lateral direction (orthogonal to the depth direction), at which an interaction has occurred between an annihilation radiation and a radiation detection element. Reference is then made to the detection time correction information to provide information regarding time-of-flight difference with improved accuracy, thereby solving the aforementioned problems.

The positron emission tomography scanner which employs information regarding a time-of-flight difference between annihilation radiations for image reconstruction can be provided with a memory in which the detection time correction information is written.

Furthermore, the radiation detection element can be a scintillator crystal which provides information regarding the depth direction at which an interaction with an annihilation radiation has occurred inside the detection element.

Furthermore, the scintillator crystal can be regarded to have a bar-like shape longer in the depth direction, and to be a plurality of virtual layers which are provided in the depth direction and stacked in two or more layers in the depth direction.

Furthermore, a scintillator crystal providing the information on the depth direction and a scintillator crystal provided with virtual layers can be stacked in two or more stages in the depth direction.

Furthermore, the detection time correction information can be used to correct for an error in detection time caused by a difference in propagation speed between an annihilation radiation in a scintillator crystal and scintillation light.

The detection time correction information can also be used to correct for an error in detection time caused by a difference in propagation path length of scintillation light in a scintillator crystal.

The detection time correction information can also be used to correct for an error in detection time resulting from the difference in output waveform of an optical detector caused by the difference in propagation path of scintillation light in a scintillator crystal.

The present invention further provides a radiation detector for detecting an annihilation radiation incident upon a radiation detection element. The radiation detector has detection time correction information for correcting for an error in detection time according to the information on the coordinates, representing the depth direction and the lateral direction, at which an interaction has occurred between an annihilation radiation and a radiation detection element.

The radiation detection element can be a scintillator crystal. The detection time correction information can be used to correct for an error in detection time caused by the difference between the flight speed of an annihilation radiation and the propagation speed of scintillation light produced in the scintillator crystal due to an interaction between the annihilation radiation and the scintillator crystal.

Furthermore, the radiation detection element can be a scintillator crystal. The detection time correction information can be used to correct for an error in detection time resulting from the output waveform of an optical detector being varied depending on each coordinates, representing the depth and lateral directions, at which an interaction has occurred between an annihilation radiation and a scintillator crystal. This can be done because a number of scintillation photons produced in the scintillator crystal due to an interaction between an annihilation radiation and a scintillator crystal arrive at the optical detector at different times through various propagation paths, so that the relation between the time and the number of photons differs depending on the aforementioned coordinates.

The present invention can be put into practice to reduce the error in radiation detection time and improve temporal resolution.

On the other hand, when a plurality of optical detectors are employed, even use of those having the same product type number would result in an error of about several tens of picoseconds due to variations in response property of individual optical detectors. Furthermore, even in the same optical detector, its central and peripheral portions often have different response properties, thereby causing an error in detection time. The coordinates at which a light emission phenomenon occurs due to an interaction between an annihilation radiation and a scintillator crystal, and correction time data corresponding to the coordinates are created. This means that a correction is to be made in consideration of the response property of one or more optical detectors at which the photons emitted at the coordinates arrive. It is thus possible to provide improved accuracy by simultaneous use of the coordinates in the lateral direction.

BRIEF DESCRIPTION OF DRAWINGS

The preferred embodiments will be described with reference to the drawings, wherein like elements have been denoted throughout the figures with like reference numerals, and wherein;

FIG. 1 shows schematic cross-sectional views of the configuration of a conventional PET scanner in 1A and a TOF-PET scanner in 1B;

FIG. 2 shows a cross-sectional view in 2A and a time chart in 2B for explaining one of the problems to be solved by the present invention;

FIG. 3 shows a cross-sectional view in 3A and a time chart in 3B and 3C for explaining another problem to be solved by the present invention;

BEST MODE FOR CARRYING OUT THE INVENTION

Embodiments of the present invention will now be described in more detail with reference to the drawings.

Figure 7:
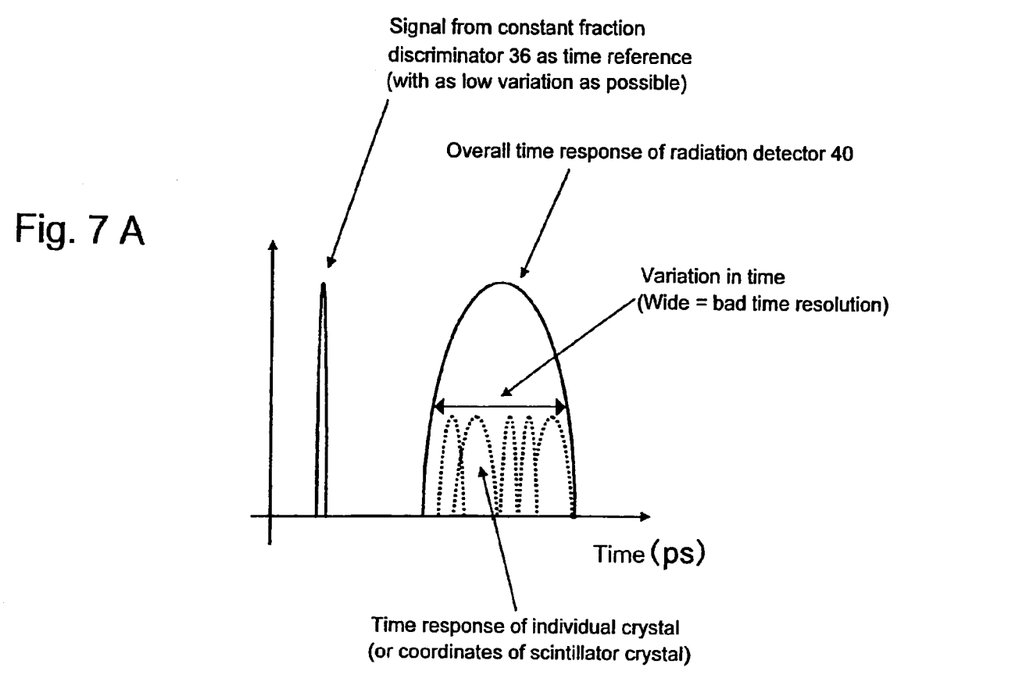
FIG. 7 is an explanatory view illustrating variations in time.

First, with reference to FIG. 7, described by way of example is a method for preparing data to be held to make a correction to errors in detection time. These errors in detection time include those caused by the difference in propagation speed between an annihilation radiation and scintillation light; the difference in propagation path length of scintillation light; and the difference in output waveform of an optical detector resulting from the difference in propagation path of scintillation light.

Figure 8:
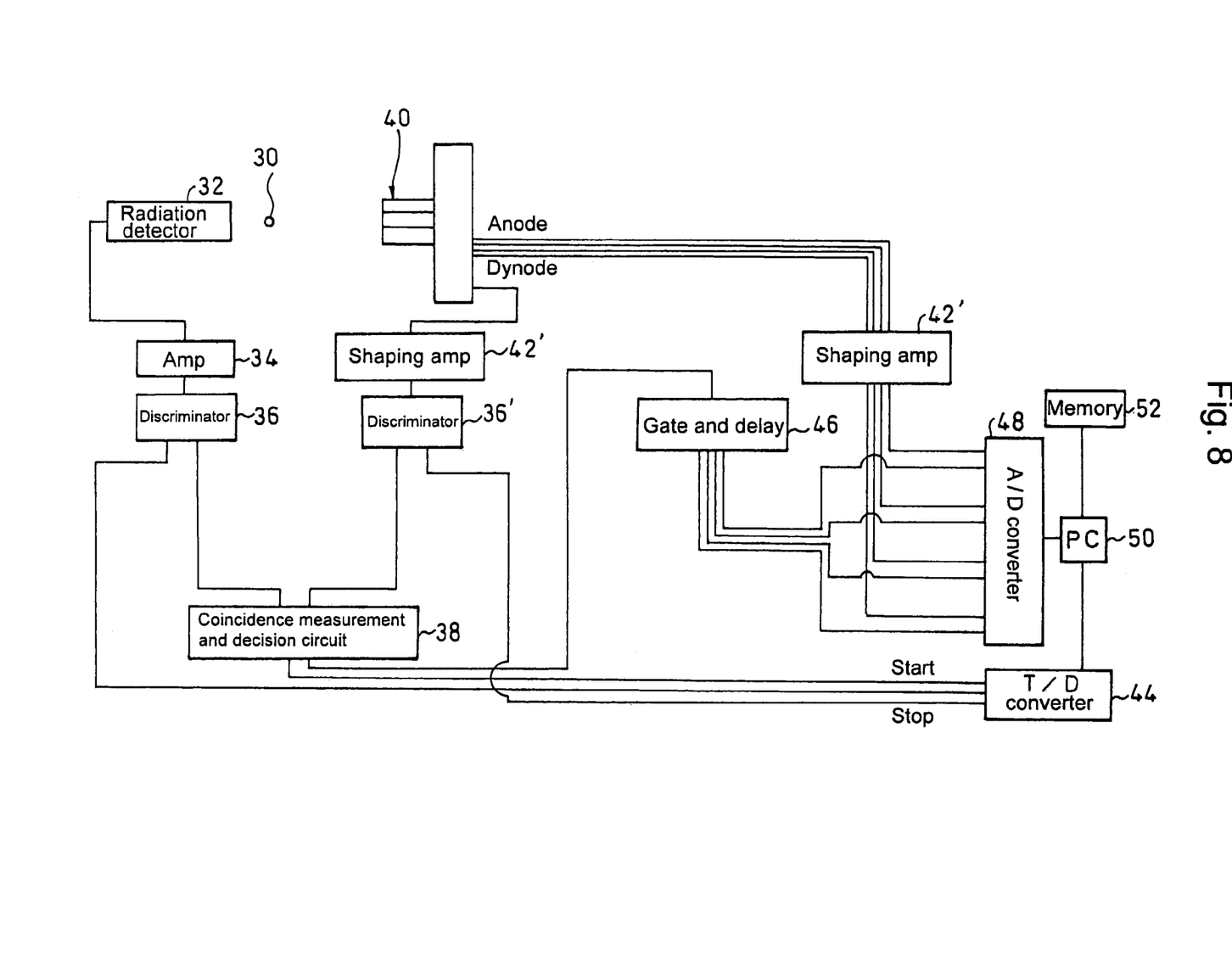
FIG. 8 is a block diagram illustrating the embodiment.

In FIG. 8, reference numeral 30 denotes a radiation source which employs a positron emitter like $^{22}$Na. Also reference numeral 32 denotes a radiation detector for measuring one of a pair of annihilation radiations of 511 keV to create a signal serving as a time reference. The radiation detector 32 includes a high-speed optical detector such as Type H3378 photomultiplier tube by Hamamatsu Photonics K.K., which incorporates a high-speed response scintillator crystal like $BaF_2$ or a plastic scintillator. Reference numeral 34 denotes an amplifier for amplifying a signal from the photomultiplier tube. The amp 34 can be eliminated when the radiation detector 32 provides a sufficiently high output. Reference numeral 36 denotes a constant fraction discriminator for generating a logic signal carrying time information based on an output signal from the radiation detector 32 or the amp 34. For example, as the discriminator 36, Type 583 by ORTEC can be employed. The output signal therefrom is sent to a coincidence measurement and decision circuit 38. Additionally, the output signal is also sent to a time-to-digital converter (also referred to as a T/D converter) 44. For example, as the T/D converter, Type 7186 by Phillips can be employed.

On the other hand, reference numeral 40 denotes a DOI radiation detector like the one shown in FIG. 5, which is used in a PET scanner that utilizes information regarding time-of-flight difference for image reconstruction. For example, the DOI radiation detector 40 is the position sensitive optical detector (PS-PMT) 21 that incorporates the crystal block 23 having scintillator crystal elements integrated in three dimensions. As described above, the PET scanner has to acquire information regarding the position of incidence, energy, and time from the output signal of the optical detector. As an example, the position sensitive optical detector 21 is a photomultiplier tube. In this case, a dynode signal is entered into a shaping amp 42 to be waveform shaped and amplified and then sent to a constant fraction discriminator 36', from which the resulting logic signal is sent to the coincidence measurement and decision circuit 38 and the time-to-digital converter 44. It should be noted that if the position sensitive optical detector 21 provides a sufficiently high output voltage, the shaping amp 42 can be eliminated.

When the coincidence measurement and decision circuit 38 has received logic signals from the constant fraction discriminators 36 and 36' within a predetermined period of time, the coincidence measurement and decision circuit 38 determines that both the signals are derived from a pair of annihilation radiations, and then directs a gate and delay generator 46 to generate a gate signal. For example, as the gate and delay generator 46, Type 416A by ORTEC can be used.

It should be noted that, when the radiation source 30 provides too frequent radiation, caution must be taken because annihilation radiations will be more likely paired erroneously in such a case.

On the other hand, an anode signal is supplied to a shaping amp 42' to be waveform shaped and amplified, and then converted into digital data indicative of the magnitude of the signal by an analog to digital converter (A/D converter) 48. The total magnitude of the summed output signals provides information on energy. Furthermore, the distribution of output signals from each anode or each optical detector is used as crystal coordinates information for identifying the scintillator crystal that has emitted light. The A/D converter 48 is active only while receiving the gate signal from the gate and delay generator 46. The data from the time-to-digital converter 44 and the A/D converter 48 is recorded and held in a memory 52 of a personal computer (PC) 50 in the form of a table. Note that if the position sensitive optical detector 21 provides a sufficiently high output voltage, the shaping amp 42' can be eliminated.

In this instance, the crystal coordinates information is determined by calculation from the information on the number and the position of multiple photons arriving at an optical detector within a certain period of time, irrespective of the time of arrival, wherein the photons have been produced in a scintillator crystal upon incidence of one annihilation radiation. In general, output signals from each electrode of the position sensitive optical detector (or a plurality of optical detectors) are integrated over a predetermined period of time, and then Anger calculation is used to find the coordinates (centre of gravity coordinates) that represent the distribution of positions of arrival of the photons. In contrast, time information is obtained by bundling all the signals from the position sensitive optical detector (or a plurality of optical detectors) irrespective of the positions of arrival and applying the aforementioned constant fraction method or the like. Since the output start time and the waveform at each electrode vary with the distribution of photons arriving at the optical detector, any signal from individual electrodes will not represent the time of incidence of annihilation radiations. The bundled signals from all electrodes will represent the time of incidence of annihilation radiation. For example, even when the position sensitive optical detector is a photomultiplier tube with a plurality of anode electrodes, but with the dynode being shared, a signal from the dynode can be used to replace the output of all the aforementioned signals bundled together.

In this instance, if the solid angle subtended by the radiation source 30 at the DOI radiation detector 40 is sufficiently small, the distance relation between the radiation detector 32, the radiation source 30, and the DOI radiation detector 40 is considered as constant in good approximation. Accordingly, the difference in arrival time between a signal sent from the radiation detector 32 through the constant fraction discriminator 36 to the time-to-digital converter 44 and a signal sent from the DOI radiation detector 40 through the constant fraction discriminator 36' to the time-to-digital converter 44 will be constant all the time. However, since an error actually occurs due to the aforementioned three types of causes, the distribution of time differences measured by the DOI radiation detector 40 has a variation width as shown in the graph to the left of FIG. 6. It should be noted that a greater variation width means that there is a greater uncertainty about the decision of the time at which a radiation is detected, whereas a smaller variation width means that the time has been determined with higher accuracy. Here, as shown in FIG. 7A on the left side, variations in response time of the radiation detector 40 indicated by a solid line include variations in response time of individual constituent scintillator crystals indicated by broken lines and an error in time. The variations in time correspond to the width of each graph in time axis indicated by the broken lines, while the error in time corresponds to the center (center of gravity) of each graph in time axis indicated by the broken lines. Here, the system of FIG. 8 serves to measure not only the graph indicated by the solid line but also the graph indicated by the broken lines for the individual scintillator crystals. It is thus possible to create a time error data table as shown at the center of FIG. 6 from the center of gravity of the individual broken-line graphs.

As shown in FIG. 7B on the right side, the error data table can be used to perform an addition or a subtraction with a correction time, thereby aligning the center of the graph of each scintillator crystal indicated by the broken lines with a certain point in time. Accordingly, the width of the response graph of the radiation detector 40 plotted as an overlap among each scintillator crystal graph indicated by the solid line, i.e., variations in time are reduced. This means that the temporal resolution of the radiation detector 40 has been improved by using the correction time data table.

It should be noted that if the solid angle subtended by the radiation source 30 at the DOI radiation detector 40 is not sufficiently small, a lead collimator is interposed between the radiation source 30 and the DOI radiation detector 40 and part of the DOI radiation detector 40 is irradiated to acquire detection time correction data. Then, it is repeatedly carried out to move the DOI radiation detector 40 so that another part thereof is irradiated to acquire detection time correction data, thereby allowing for constructing more accurate detection time correction data.

The detection time correction according to the present invention can be made by allowing the PC 50 to acquire time data from the time-to-digital converter 44 and then perform an addition or a subtraction with the time while referring to the memory 52.

It should be noted that, although a delay circuit for providing delayed signals is eliminated for simplicity purposes in FIG. 8, it is necessary to adjust, as appropriate, delays in time caused at each circuit. For example, when the response of the radiation detector 32 is earlier than the response of the DOI radiation detector 40, a delay circuit may be interposed between the amp 34 and the constant fraction discriminator 36. On the other hand, when a signal from the coincidence measurement and decision circuit 38 to start the time-to-digital converter 44 arrives there later than at the constant fraction discriminators 36 and 36', a delay circuit may be interposed between the time-to-digital converter 44 and the constant fraction discriminator 36 and 36', respectively. The delay circuit is to provide delayed signals and not to increase or reduce the range of an error in time.

In this embodiment, data to correct for all the three causes of error was acquired at a time. This is more preferable rather than acquiring it individually because the causes may conceivably work in combination constructively or destructively.

The radiation detector thus having obtained the detection time correction information may be disposed, e.g., as shown in FIG. 1B, to be used together with the detection time correction information, thereby providing a TOF-PET scanner which enables image reconstruction with improved time-of-flight difference accuracy. It should be noted that the timing among the radiation detectors is adjusted in the same manner as the conventional PET scanner that does not use information on time-of-flight difference. The present invention is intended to improve the performance of a PET scanner, which uses information regarding time-of-flight difference for image reconstruction, by sufficiently adjusting the timing among the radiation detectors and then correcting for the detection time provided inside the individual radiation detectors.

It should be noted that the aforementioned embodiment is an example of the present invention and is not intended to limit the scope of the claims of the present invention. For example, as described above, data may be recorded in a hardware storage device to then use a personal computer or the like to make corrections by software.

Further, a correction may be made to the three causes of error collectively or to the respective causes individually. For example, the difference in propagation speed between an annihilation radiation and scintillation light can be determined by calculation if the refractive index of the scintillator crystal is known. More specifically, the error in detection time caused by the difference in propagation speed between an annihilation radiation and scintillation light is $(n-1) \times d/c$, where n is the refractive index of the scintillator crystal, d is the distance between the location of emission in the scintillator crystal and the optical detector, and c is the propagation speed of light in a vacuum.

Furthermore, as for the difference in output waveform of an optical detector caused by the difference in propagation path of scintillation light, the waveforms can be sampled after having been converted from analog to digital. The digital processing of the waveforms makes it possible to reduce the error in detection time (see A. Mann et al, IEEE Trans., Nucl. Sci., Vol. 53, No. 1, pp. 297 to 303, 2006).

It should be noted that even one of the three causes of error can be corrected for to improve the temporal resolution by the amount of the cause of error removed. Thus, two causes of error may be more preferably corrected for, and most preferably all the three causes of error may be corrected for.

Figure 9:
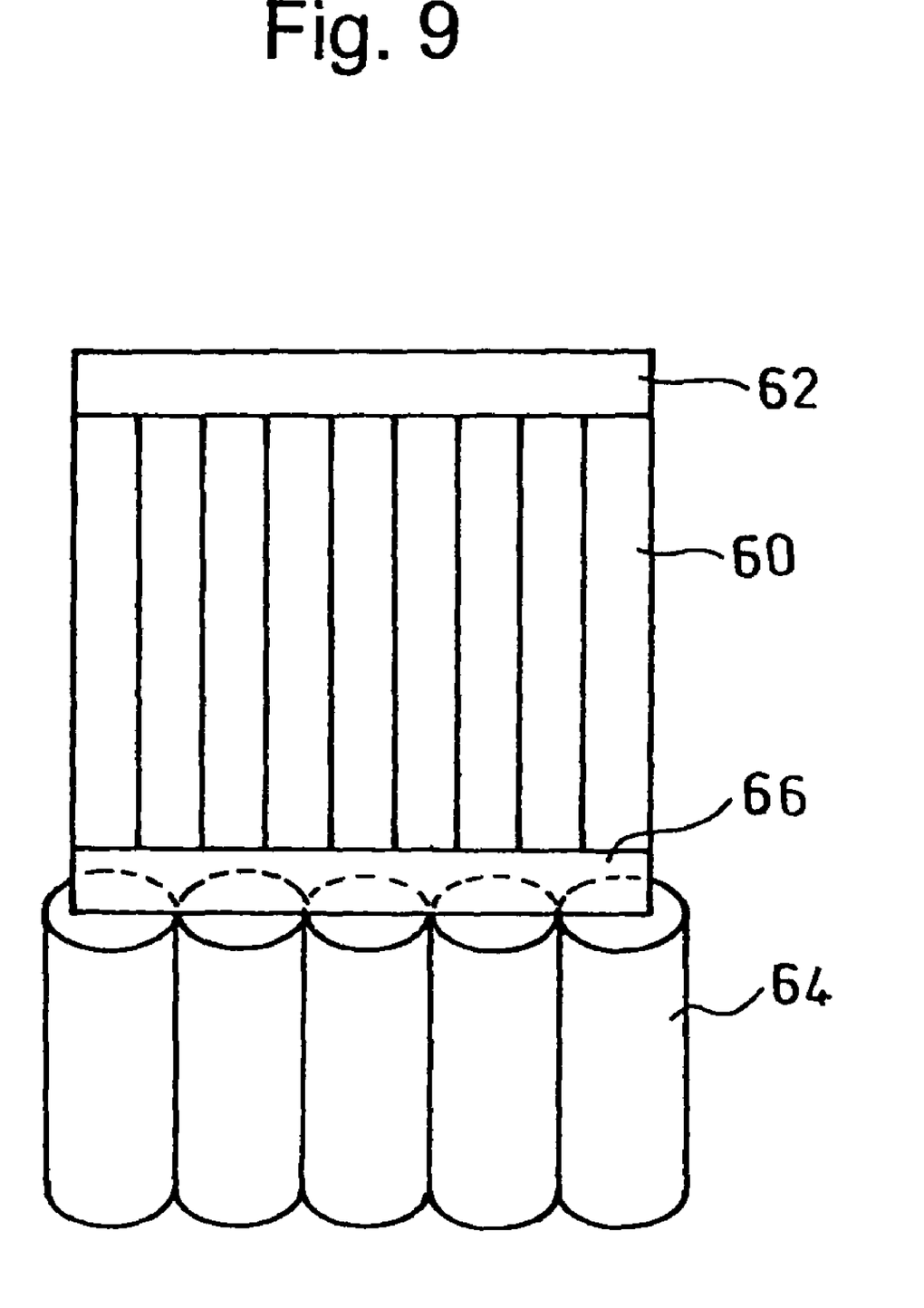
FIG. 9 is a view illustrating the configuration of a modified example of a radiation detector.

On the other hand, the scintillator crystal is not always required to be stacked in layers in the depth direction. For example, such a technique is known that is applicable to a long crystal of several centimeters. In this technique, as illustrated by way of example in FIG. 9, an avalanche photodiode (APD) 62 is disposed as an optical detector on the top surface of a comb-shaped scintillator crystal 60 and a photomultiplier tube (PMT) 64 is disposed on the bottom surface. From the ratio between the outputs from both the optical detectors, the information on the location of emission along the depth at which an interaction occurs between an annihilation radiation and the scintillator crystal (see Y. Shao et al, IEEE Trans., Nucl. Sci., Vol. 49, No. 3, pp. 649 to 654, 2002). The avalanche photodiode 62 may be used to prepare an optical detector less than 1 millimeter in thickness, and thus provides a sufficiently small probability of absorbing or scattering annihilation radiation.

The present invention presents the concept for correcting for an error in detection time by obtaining information on the coordinates in a scintillator crystal at which an interaction between an annihilation radiation and the crystal occurs, and is thus applicable even to those scintillator crystals that are shaped, sized, or arranged differently. For example, when crystals are not stacked in layers, a crystal, which has a typical length of several centimeters, may be virtually divided into m layers (m is any natural number), and data may be prepared for each virtual region to correct time. On the other hand, when m is sufficiently large, the data may be substantially continual correction data. In contrast, when m is smaller as compared with the resolution of information regarding the location of emission along the depth, interpolative data can be created, thereby reducing error.

Furthermore, for example, an optical detector such as a silicon photomultiplier, an APD operated in Geiger mode (see the silicon photomultiplier, V. Saveliev, Nucl. Instrum. Methods, Phys. Res. A, Vol. 535, pp. 528 to 532, 2004), may be interposed between each layer of the scintillator block shown in FIG. 5, and each scintillator crystal may be divided into virtual layers. In this case, an emission can be located not only at a particular crystal but also at a depth in that crystal, thereby correcting for error in detection time with improved accuracy.

The optical detector is not limited to a photomultiplier tube. For example, new optical detectors may also be employed such as an avalanche photodiode or a silicon photomultiplier. Furthermore, the optical detector may be of a position sensitive type (e.g., Type H9500 photomultiplier tube by Hamamatsu Photonics K.K.), or of a non-position sensitive type. Furthermore, a light guide 66 as shown by way of example in FIG. 9 or optical fiber may also be interposed between a scintillator crystal and an optical detector. Furthermore, a plurality of types of optical detectors may also be used in combination.

Furthermore, a sheet of reflective material such as polymer mirror film (e.g., ESR multi polymer mirror by 3M) or Teflon (registered trade mark), or a white powder reflective material such as titanium oxide may be interposed between a scintillator crystal and a crystal. Alternatively, a medium transparent to scintillation light, such as silicon grease, acrylic resin, or air, may be used. Further, crystals may be adhered to each other using an adhesive transparent to scintillation light (e.g., Type KE420 RTV rubber by Shin-Etsu Silicon).

It should be apparent to those skilled in the art that the above-described embodiments are merely illustrative which represent the application of the principles of the present invention. Numerous and varied other arrangements can be readily devised by those skilled in the art without departing from the spirit and the scope of the invention.

INDUSTRIAL APPLICABILITY

The present invention can be used in a positron emission tomography (PET) scanner which uses information on the time-of-flight difference between the two annihilation radiations for image reconstruction, and in a radiation detector.

The invention claimed is:

1. A positron emission tomography scanner which employs information regarding a time-of-flight difference between annihilation radiations for image reconstruction, comprising;
    a radiation detection element, that is a scintillator crystal which provides information regarding the depth direction at which an interaction with an annihilation radiation has occurred inside the detection element,
    means for holding detection time correction information corresponding to information on coordinates, representing a depth direction and a lateral direction, at which an interaction has occurred between an annihilation radiation and the radiation detection element, and;
    means for correcting the detection time by referring to the detection time correction information so that information accuracy regarding the time-of-flight difference is improved.

2. The positron emission tomography scanner according to claim 1, wherein the means for holding the detection time correction information is a memory.

3. The positron emission tomography scanner according to claim 1, wherein the scintillator crystal is regarded to have a bar-like shape longer in the depth direction, and to be a plurality of virtual layers which are provided in the depth direction and stacked in two or more layers in the depth direction.

4. The positron emission tomography scanner according to claim 1, wherein the scintillator crystal is stacked in two or more stages in the depth direction.

5. The positron emission tomography scanner according to claim 1, wherein the means for correcting the detection time is used to correct for an error in detection time caused by a difference in propagation speed between an annihilation radiation in the scintillator crystal and scintillation light.

6. The positron emission tomography scanner according to claim 1, wherein the means for correcting detection time is used to correct for an error in detection time caused by a difference in propagation path length of scintillation light in the scintillator crystal.

7. The positron emission tomography scanner according to claim 1, wherein the means for correcting the detection time is used to correct for an error in detection time resulting from a difference in output waveform of a detector caused by a difference in propagation path of scintillation light in the scintillator crystal.

8. A radiation detector for detecting an annihilation radiation incident upon a radiation detection element that is a scintillator crystal which provides information regarding the depth direction at which an interaction with an annihilation radiation has occurred inside the detection element, having a means for correcting detection time for correcting an error in detection time according to information on coordinates, representing a depth direction and a lateral direction, at which an interaction has occurred between an annihilation radiation and a radiation detection element.

9. The radiation detector according to claim 8, wherein:
    means for correcting the detection time is used to correct for an error in detection time caused by a difference between a flight speed of the annihilation radiation and a propagation speed of scintillation light produced in the scintillator crystal due to an interaction between the annihilation radiation and the scintillator crystal.

10. The radiation detector according to claim 8, wherein:
    the means for correcting the detection time is used to correct for an error in detection time resulting from an output waveform of an optical detector being varied depending on each coordinates, representing a depth direction and a lateral direction, at which an interaction has occurred between the annihilation radiation and the scintillator crystal, because a number of scintillation photons produced in the scintillator crystal due to the interaction between the annihilation radiation and the scintillator crystal arrive at the optical detector at different times through various propagation paths, so that the relation between time and the number of photons differs depending on the coordinates.

* * * * *